United States Patent [19]

Aho

[11] Patent Number: 4,584,787
[45] Date of Patent: Apr. 29, 1986

[54] HEATED HANDLE STRUCTURE

[76] Inventor: Robert E. Aho, R.D. 2, Box 74, Brockway, Pa. 15824

[21] Appl. No.: 724,302

[22] Filed: Apr. 17, 1985

[51] Int. Cl.$^4$ .................. A01K 87/00; A61F 7/06
[52] U.S. Cl. ........................................ 43/23; 126/204; 126/206
[58] Field of Search .................... 43/23; 126/204, 206, 126/208

[56] References Cited

U.S. PATENT DOCUMENTS

| 2,835,245 | 5/1958 | Morgan | 126/208 |
| 2,997,042 | 8/1961 | Mitchell | 43/23 X |
| 4,286,571 | 9/1981 | Hung | 126/206 |

FOREIGN PATENT DOCUMENTS

| 66836 | 1/1914 | Switzerland | 126/206 |
| 366362 | 2/1932 | United Kingdom | 126/204 |

Primary Examiner—Nicholas P. Godici
Assistant Examiner—Carmine Cuda
Attorney, Agent, or Firm—Harvey B. Jacobson

[57] ABSTRACT

A heated handle structure for a fishing rod comprises an outer cylindrical container attached to the end of the rod, an inner cylindrical container for receiving a solid fuel stick, the inner container being rotatably mounted in the outer container, registrable vents in the respective container walls, the degree of opening of which is adjusted by relative rotation of the containers in order to vary the amount of heat supplied by the fuel stick, and a spring-loaded adjustment mechanism between the containers for releasably retaining them in selected angular positions of adjustment.

17 Claims, 7 Drawing Figures

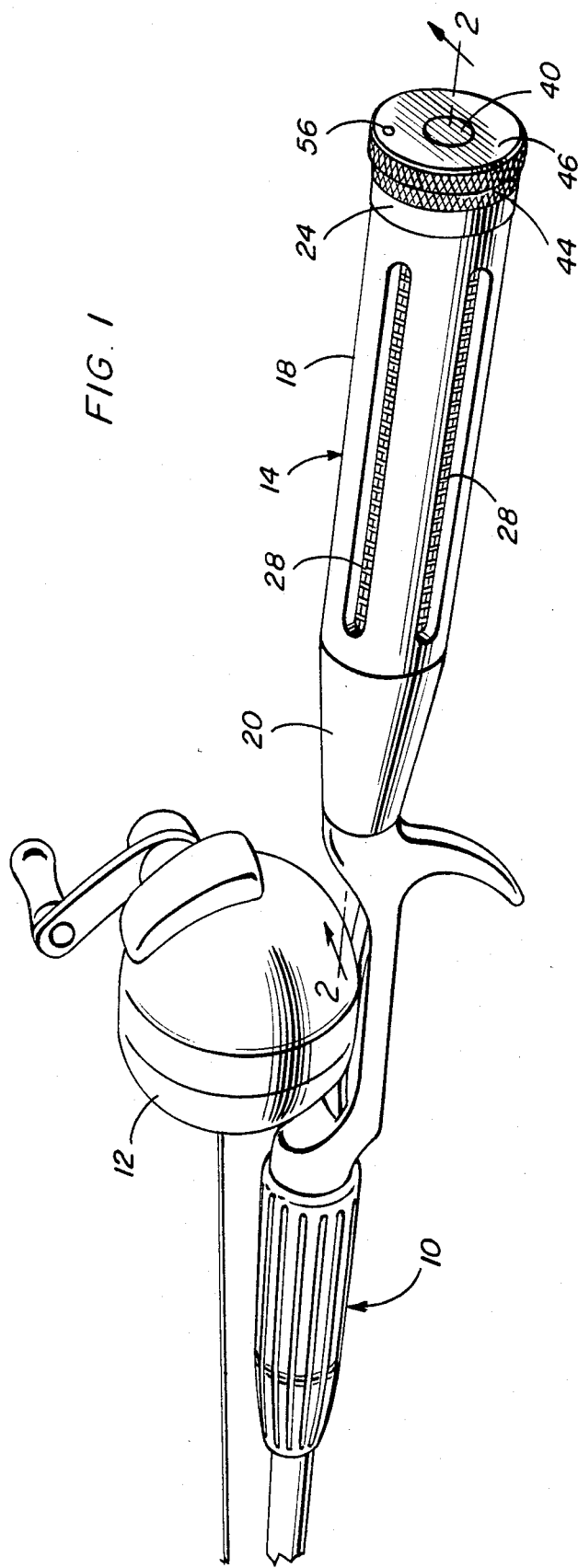
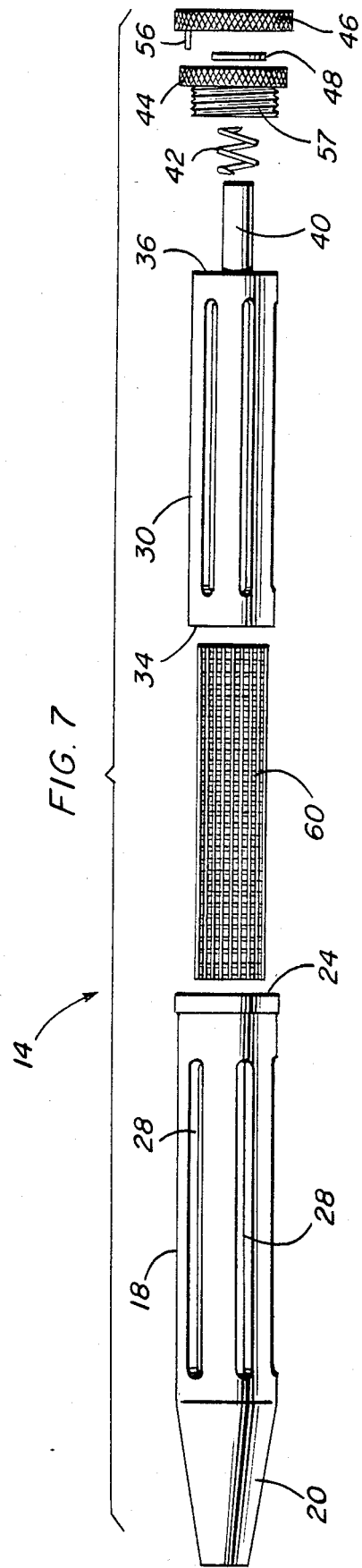

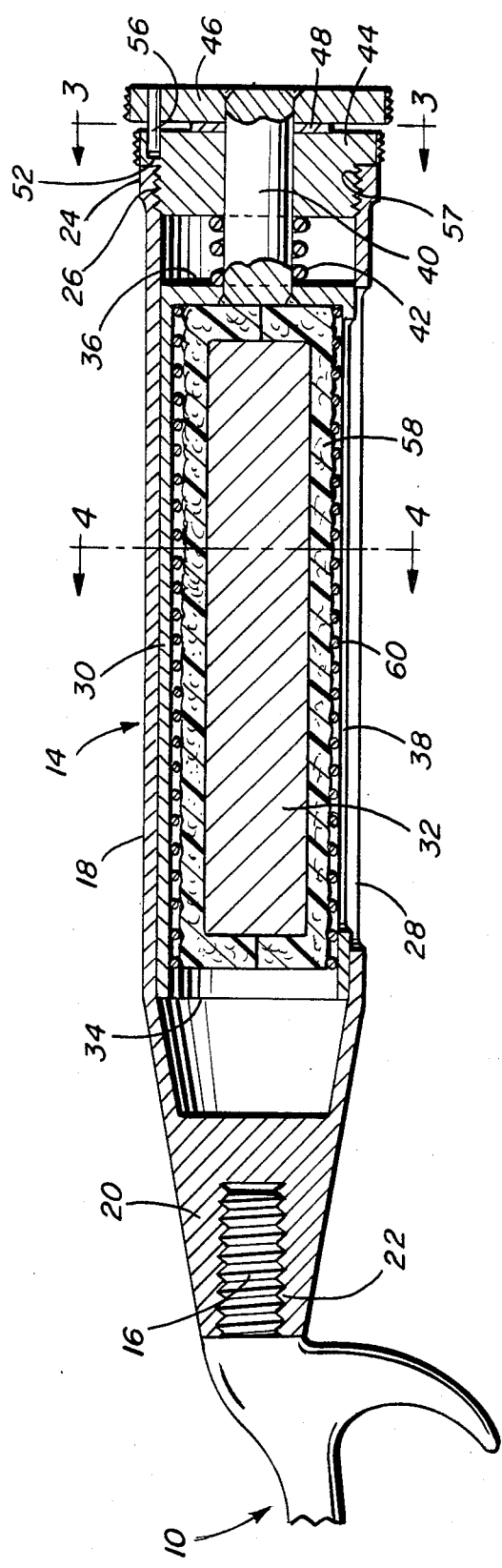
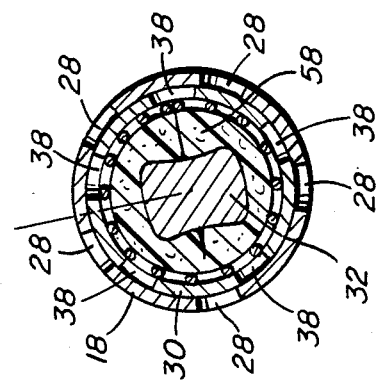
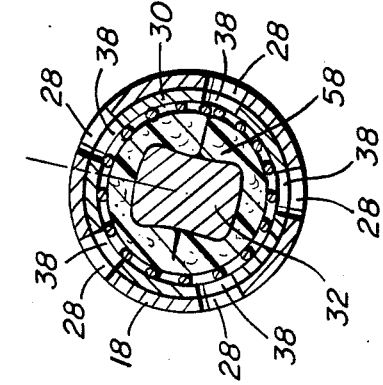
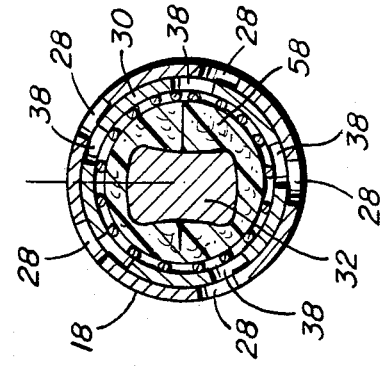
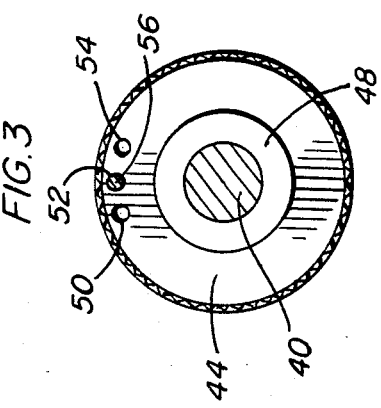

HEATED HANDLE STRUCTURE

BACKGROUND OF THE INVENTION

This invention relates to a hand-warming structure which may be incorporated, for example, in a handle for a fishing rod or the like to enable a user to keep his or her hands warm while fishing in cold weather. The structure, however, may also be used in other hand-warming applications.

Objects of the invention include, for example, the provision of a hand-warming structure suited for use with solid fuel sticks, which is simple to load and operate, which has a facility for adjusting the heat output, and which presents a minimal fire hazard.

STATEMENT OF PRIOR ART

Applicant is aware of the following U.S. Patents pertaining to hand warmer structures and the like. None of these, however, discloses a structure having the features of the present invention.

U.S. Pat. No. Re. 24,858—8-9-60
U.S. Pat. No. 2,816,539—12-17-57
U.S. Pat. No. 2,835,245—5-20-58
U.S. Pat. No. 2,997,042—8-22-61
U.S. Pat. No. 3,577,974—5-11-71

SUMMARY OF THE INVENTION

A hand warmer structure in accordance with the invention comprises an outer cylindrical container having a closed front end, an open back end, and vent means in the circumferential wall thereof, an inner cylindrical container for coaxial conforming receipt in the outer container from the back end of the outer container, the inner container being adapted to retain a solid fuel element therein and having vent means in the circumferential wall thereof registrable with the vent means of the outer container upon relative rotary adjustment of the containers about their common axis, an end cap for the open end of the outer container, a shaft extending from the back end of the inner container through the end cap and terminating in an adjustment knob for rotating the inner container in the outer container to adjust the relative alignment between the respective vent means between a fully open position for maximum air admission to the fuel element and a fully closed position for excluding air from the fuel element, and retention means for retaining the knob and the inner container in selected angular position relative to the outer container.

The retention means may comprise positive engagement means between the knob and the end cap, such as a pin on the knob and angularly displaced receiving holes in the end cap for the pin, along with a coil spring received on the shaft for urging the pin into engagement in a selected hole, so that in order to adjust the degree of opening of the vent means, the knob is withdrawn axially against the spring pressure, rotated to align the pin with a selected hole in the end cap, and released. The structure may be in the form of an elongate handle for a fishing rod, with a connection for a rod or the like at the front end of the outer container. The device may use fuel elements in the form of readily available solid fuel sticks which may be wrapped in glass wool or the like in a surrounding flame-retarding mesh sleeve which is received in the inner container, solid fuel elements being safer to use than liquid fuel. The structure is readily dismantled by removal of the end cap (which may be threaded onto the back end of the outer container) for replacing and lighting the fuel element.

These together with other objects and advantages which will become subsequently apparent reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

FIG. 1 is a perspective view of part of a fishing rod including a heated handle structure in accordance with the invention.

FIG. 2 is an enlarged sectional view on line 2—2 of FIG. 1.

FIG. 3 is a sectional view on line 3—3 of FIG. 2.

FIG. 4 is a sectional view on line 4—4 of FIG. 2.

FIGS. 5 and 6 are views similar to FIG. 4 showing the structure in different positions of adjustment.

FIG. 7 is an exploded elevational view of the handle structure.

DESCRIPTION OF PREFERRED EMBODIMENT

Referring initially to FIGS. 1 and 2, there is shown the back portion of a fishing rod 10 having a reel 12 and a heated handle structure 14 in accordance with the invention threaded onto a screw shank 16 on the back of the rod, for enabling a fisherman to warm his hands in cold weather.

Handle structure 14 includes a cylindrical outer container 18 of suitable metal having a solid front end 20 of tapered profile formed with a tapped hole 22 for threading onto shank 16. The back end 24 of container 18 is open and formed with an internal thread 26. The cylindrical wall of container 18 is provided with circumferentially spaced longitudinal vent openings 28.

An inner cylindrical container 30 which may be of like material to container 18, is provided to receive a solid fuel stick 32 as will be described, and to fit closely and coaxially inside container 18. Inner container 30 has an open front end 34, a closed back end 36, and circumferentially spaced longitudinal vent openings 38. It may here be stated that container 30 can be rotatably adjusted within container 18 in order to adjust the relative positions of the respective sets of vent openings between a first position (FIG. 5) where the respective sets are in register (maximus opening) a second position (FIG. 6) where they are wholly out of register (fully closed) and a third intermediate position (FIG. 4) where they are in partial register.

A stub-shaft 40 is secured to the back end of container 30 with a coil spring 42 and an end cap 44 loosely received on the shaft. An adjustment knob 46, which may have a knurled or serrated periphery, is secured to the end of shaft 40, as by welding, with a washer 48 between the knob and the end cap. As shown in FIG. 3, three circumferentially spaced holes 50, 52, 54 are formed in end cap 44 selectively to receive a pin 56 extending from the under surface of knob 46. End cap 44 has an external thread 57 for engaging with internal thread 26 of container 18. It is understood that spring 42 acting between the back end of container 30 and end cap 44, urges pin 56 into one or other of holes 50–54. The inner container can, however, be rotated relative to end cap 44 by pulling knob 46 outwardly against the spring pressure, and disengaging the pin. In this manner, the pin can be moved from hole to hole.

The interior of container 30 is shaped to receive a standard, commercially available solid fuel stick 32, surrounded by glass wool 58 or the like, and received in an outer steel mesh fire-retarding sleeve 60 which is a close fit in container 30.

To load the handle structure with a fresh fuel stick, the inner container 30 is removed from the outer container simply by unthreading the end cap 44. The fuel stick can then be removed and replaced with a freshly lighted fuel stick. The structure is then reassembled simply by inserting the inner container into the outer container and threading the end cap into the outer container. When the end cap is threaded fully home, the alignment of the respective sets of vent openings 28 and 38 will be as shown in one of FIGS. 4 to 6. The degree of opening of the vent openings can then be adjusted, as required, by moving pin 56 as between the respective holes 50-54 by pulling on and rotating knob 46. When the vent openings are fully opened (FIG. 5) maximum air is admitted to the fuel stick for rapid combustion and maximum heating. When the vent openings are partially open (FIG. 4) there is less air available, thereby reducing the heat output, and when the vent openings are closed (FIG. 6) air is excluded and the fuel stick is extinguished.

It will be understood that the described handle structure provides a hand-warming device which can be used in diverse applications in addition to its use as a handle for a fishing rod. It is safer than a liquid fuel device, and simple to operate with the pin and hole assembly providing a simple-to-use positive engagement-type adjusting mechanism for varying the heat outward of the structure.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as new is as follows:

1. A hand warmer structure comprising an outer cylindrical container having a closed front end, an open back end, and vent means in the circumferential wall thereof, an inner cylindrical container for coaxial conforming receipt in the outer container from the back end of the outer container the inner container an a closed back end having an open front end for inserting a fuel element into the inner container, and having vent means in the circumferential wall thereof registrable with the vent means in the outer container upon relative rotary adjustment of the containers about their common axis, an end cap for securing on the open end of the outer container, a shaft extending from the back end of the inner container through the end cap and terminating in an adjustment knob for rotating the inner container in the outer container to adjust the relative alignment between the respective vent means between a fully open position for maximum air admission to the fuel element, and a fully closed position for excluding air from the fuel element, and retention means for retaining the knob and the inner container in selected angular position relative to the outer container.

2. The invention of claim 1 wherein the retention means comprises positive engagement means on the end cap and adjustment knob respectively for holding the inner container in a selected one of a plurality of angular positions relative to the outer container adjusting the degree of opening of the vent means.

3. The invention of claim 2 wherein the positive engagement means comprises a pin on one of the end cap and knob engageable in a selected one of a plurality of circumferentially spaced holes in the other of the end cap and knob, and a spring means acting between the end cap and knob urging the pin toward engagement in a respective hole whereby adjustments of the degree of opening of the vent means are effected by pulling the knob outwardly against pressure exerted by the spring means to disengage the pin from one of the holes, and rotating and releasing the knob to engage the pin in another of the holes.

4. The invention of claim 3 wherein the pin, holes and vent means are mutually configured for providing maximum opening of the vent means when the pin is engaged in one of the holes, partial opening of the vent means when the pin is engaged in another of the holes, and closure of the vent means when the pin is engaged in a third of the holes.

5. The invention of claim 1 wherein the respective vent means comprises circumferentially spaced elongate slots in the respective containers.

6. The invention of claim 1 wherein the back end of the outer container is internally threaded and the end cap has a complimentary external thread for securing the end cap on the outer container by threaded engagement of the respective threads.

7. The invention of claim 1 wherein the front end of the outer container includes means for attaching the structure to a fishing rod to form a heated handle for the rod.

8. The invention of claim 7 wherein the attaching means comprises a tapped hole in the front end of the outer container for threading onto a screw shank in back of the fishing rod.

9. The invention of claim 1 including a fire-retarding cylindrical mesh sleeve for insertion in the inner container and for receiving the fuel element therein.

10. The invention of claim 9 wherein the fuel element is a solid fuel stick.

11. The invention of claim 10 including a surrounding layer of glass wool between the fuel stick and the mesh sleeve.

12. A fishing rod having a handle structure comprising an outer cylindrical member having an open back end and vent means in the circumferential wall thereof, an inner cylindrical container for coaxial conforming receipt in the outer cylindrical member, the inner container having an open front end for insertion of a fuel element into the inner container and a closed backend and having vent means in the circumferential wall thereof registrable with the vent means of the outer cylindrical member upon relative rotary adjustment of the inner container about its axis, an end cap for securing on the open end of the outer member, a shaft extending from the back end of the inner container through the end cap and terminating in an adjustment knob for rotating the inner container in the outer member to adjust the relative alignment between the respective vent means between a fully open position for maximum air admission to the fuel element, and a fully closed position for excluding air from the fuel element, and retention means for retaining the knob and the inner container in selected angular position relative to the outer member.

13. The invention of claim 12 wherein the retention means comprises positive engagement means on the end cap and adjustment knob respectively for holding the inner container in a selected one of a plurality of angular positions relative to the outer member adjusting the degree of opening of the vent means.

14. The invention of claim 13 wherein the positive engagement means comprises a pin on one of the end cap and knob engageable in a selected one of a plurality of circumferentially spaced holes in the other of the end cap and knob, and a spring means acting between the end cap and knob urging the pin toward engagement in a respective opening whereby adjustments of the degree of opening of the vent means are effected by pulling the knob outwardly against pressure exerted by the spring means, to disengage the pin from one of the holes and rotating and releasing the knob to engage the pin in another of the holes.

15. The invention of claim 12 including a fire-retarding cylindrical mesh sleeve for insertion in the inner container and for receiving the fuel element therein.

16. The invention of claim 15 wherein the fuel element is a solid fuel stick.

17. The invention of claim 16 including a surrounding layer of glass wool between the fuel stick and the mesh sleeve.

* * * * *